United States Patent
Liger et al.

(10) Patent No.: US 9,119,889 B2
(45) Date of Patent: Sep. 1, 2015

(54) COMPACT SYSTEM FOR STERILIZATION BY BOMBARDMENT OF ELECTRONS

(71) Applicant: Getinge La Calhene, Vendome (FR)

(72) Inventors: Philippe Liger, Gif-sur-yvette (FR); Patrick Clech, Sainville (FR)

(73) Assignee: GETINGE LA CALHENE, Vendome (FR)

(*) Notice: Subject to any disclaimer, the term of this patent is extended or adjusted under 35 U.S.C. 154(b) by 0 days.

(21) Appl. No.: 14/389,552

(22) PCT Filed: Mar. 29, 2013

(86) PCT No.: PCT/EP2013/056821
§ 371 (c)(1),
(2) Date: Sep. 30, 2014

(87) PCT Pub. No.: WO2013/149968
PCT Pub. Date: Oct. 10, 2013

(65) Prior Publication Data
US 2015/0069264 A1    Mar. 12, 2015

(30) Foreign Application Priority Data
Apr. 2, 2012  (FR) ..................... 12 53006

(51) Int. Cl.
 *A61L 2/08* (2006.01)
 *A61L 2/14* (2006.01)
(52) U.S. Cl.
 CPC . *A61L 2/087* (2013.01); *A61L 2/14* (2013.01); *A61L 2202/122* (2013.01)
(58) Field of Classification Search
 CPC ..... H01J 37/30; H01J 37/3002; H01J 37/301; H01J 37/317; A61L 2/03; A61L 2/087; A61L 2/24
 USPC ................ 250/453.11–455.11, 492.3; 422/22
 See application file for complete search history.

(56) References Cited

U.S. PATENT DOCUMENTS

| 7,459,706 | B2 * | 12/2008 | Fontcuberta et al. ...... 250/492.3 |
| 7,626,186 | B2 * | 12/2009 | Kang et al. ................. 250/492.3 |
| 2008/0193341 | A1 * | 8/2008 | Fontcuberta et al. ......... 422/186 |
| 2012/0168642 | A1 * | 7/2012 | Neuschwander et al. ........................ 250/455.11 |

FOREIGN PATENT DOCUMENTS

| EP | 1 685 853 A1 | 8/2006 |
| EP | 1 849 746 A1 | 10/2007 |
| WO | 2004/102587 A2 | 11/2004 |
| WO | 2006/111681 A2 | 10/2006 |

OTHER PUBLICATIONS

Search Report issued in corresponding French Patent Application No. FR 1253006 dated Dec. 21, 2012.
International Search Report issued in Application No. PCT/EP2013/056821 dated Jun. 21, 2013.
Written Opinion issued in Application No. PCT/EP2013/056821 dated Jun. 21, 2013.

* cited by examiner

*Primary Examiner* — Jack Berman
*Assistant Examiner* — David E Smith
(74) *Attorney, Agent, or Firm* — Pearne & Gordon LLP (57) ABSTRACT

System for sterilization of objects (B) by electron bombardment comprising a chamber (2) provided with an inlet (4) and an outlet (6) through which objects (B) are input and output, said system between the inlet (4) and the outlet (6) comprising a treatment zone (II), a routing zone (I) upstream from the treatment zone (II) and an evacuation zone (III) downstream from the treatment zone (II), and means of conveying objects (B) from the inlet (4) to the outlet (6), the treatment zone (II) comprising at least one electron accelerator and a conveyor (9), the routing zone (I) and the evacuation zone (III) each including at least one radiation shielding wall (16) protecting against ionizing radiation and means allowing objects (B) to pass over the radiation shielding wall (16) passing over the top of said radiation shielding wall (16).

14 Claims, 5 Drawing Sheets

COMPACT SYSTEM FOR STERILIZATION BY BOMBARDMENT OF ELECTRONS

TECHNICAL FIELD AND PRIOR ART

This invention relates to a compact system for sterilization by electron bombardment.

For example, sterilization by bombardment of electrons is used to sterilise objects that will be introduced into a sterile isolator used in the fabrication of pharmaceutical products.

The system comprises a conveyor that will be used to transport objects to be sterilised as far as a treatment zone in which they will be irradiated by a beam generated by one or several electron accelerators and then as far as the outlet from the system which may for example be directly connected to the isolator.

Baffles formed by vertical lead plates are formed upstream and downstream from the treatment zone, so that ionising radiation generated by the electron accelerators remains confined inside the treatment zone. The conveyor that moves in a horizontal plane is then configured to go around the lead plates.

The system functions very satisfactorily and ionising radiation is confined. However, this system has a large footprint. The path that has to be travelled due to the baffles makes the conveyor large.

PRESENTATION OF THE INVENTION

Consequently, one purpose of this invention is to provide a compact sterilization system by electron bombardment.

The purpose of this invention is achieved by an electron bombardment sterilization system comprising a treatment zone, a routing zone upstream from the treatment zone and an evacuation zone downstream from the treatment zone, the routing zone and the evacuation zone each comprising a radiation shielding wall, the routing zone and/or the evacuation zone comprising a first conveyor upstream from the radiation shielding wall and a second conveyor downstream from the radiation shielding wall and means of displacing an object routed by the first conveyor to the second conveyor above the first radiation shielding wall.

Preferably, the routing zone and the evacuation zone each comprises two conveyors and means of passing objects over the radiation shielding wall.

In other words, routing of objects to be sterilised upstream and/or downstream from the treatment zone no longer takes place in a horizontal plane, but also in a vertical plane, the upstream and/or downstream conveyors are replaced by two simple shaped conveyors circulating upstream and downstream from the radiation shielding wall. The conveyors are smaller and they are easier to manufacture. The length and the transverse dimension of the upstream and downstream zones are thus reduced.

Very advantageously, the means of displacing the object from one conveyor to the other comprise an arm capable of rotating about a horizontal axis and a clamp. The clamp picks up the object and the rotating arm displaces the object from one conveyor to the next, and the clamp is then moved away to release the object.

Preferably, a logic controller controls the treatment means of objects and the routing zone devices.

The main subject-matter of this invention is then a system for sterilization of objects by electron bombardment comprising a shielded chamber to confine ionising radiation provided with an inlet and an outlet through which objects are input and output respectively, said system between the inlet and the outlet comprising a treatment zone, a routing zone upstream from the treatment zone and an evacuation zone downstream from the treatment zone, and means of conveying objects from the inlet to the outlet, the treatment zone comprising at least one electron accelerator and a conveyor, the routing zone and the evacuation zone each including at least one radiation shielding wall protecting against ionising radiation and conveyors, and in which the routing zone and/or the evacuation zone comprise at least a first and a second conveyor on each side of the radiation shielding wall and a device for crossing said radiation shielding wall allowing objects to pass over the top of said radiation shiepinslding wall.

Preferably, the routing zone and the evacuation zone each comprises at least one first and second conveyor on each side of the radiation shielding wall and a device for crossing over said radiation shielding wall so that objects can pass over the radiation shielding wall above said radiation shielding wall.

In one particularly advantageous example, the crossing means comprise an arm mounted at a first longitudinal end on a shaft capable of rotating about an axis perpendicular to a displacement direction of the objects, said axis being contained in a plane located between the first and the second conveyor, means of gripping the objects mounted on a second longitudinal end of the arm, means of rotating the arm such that it pivots between an end of the first conveyor and an end of the second conveyor and means of actuating the gripping means.

The crossing means advantageously comprise means such that the gripping means move in a succession of horizontal planes. Said means may comprise a first fixed pulley in which the rotation shaft rotates freely, a second pulley mounted free to rotate on the second longitudinal end of the arm, a belt connecting the first and second pulleys. The gripping means are fixed in rotation to the second pulley.

For example, the gripping means include a support, two jaws, said jaws being hinged free to rotate on the support, each about an axis parallel to the displacement direction, and elastic return means bringing the jaws back towards each other.

Advantageously, the actuation means are not supported by the arm.

For example, the actuation means comprise an actuation part located at the end of the first conveyor and an actuation part located at the end of the second conveyor. Each actuation part may comprise a shaft free to rotate perpendicular to the displacement direction, said shaft being fitted with two cams, each cam being designed to cooperate with each jaw to provoke pivoting of said jaws about their axis of rotation and means of rotating the shafts by a given angle.

In one example, each jaw comprises two pins located at each end of said jaw, said pins having a parallel axis distinct from the rotation axis of the jaw that supports it, each cam coming into contact with a pin by rotation of the shaft.

The means of rotating the shafts by a given angle are advantageously formed by rotating pneumatic jacks connected to the shafts by rod transmission systems.

The objects may comprise two ribs and each jaw comprises a groove in which a rib will fit. For example, the objects are boxes with a rectangular section.

The sterilization system preferably comprises means of detecting the position of objects inside each of the zones. The sterilization system advantageously comprises a logic controller controlling the crossing device(s) and treatment of objects by irradiation. For example, the conveyors may be chain link or roller belts.

BRIEF DESCRIPTION OF THE DRAWINGS

This invention will be better understood after reading the following description and appended drawings in which.

DETAILED PRESENTATION OF PARTICULAR EMBODIMENTS

Figure 1:
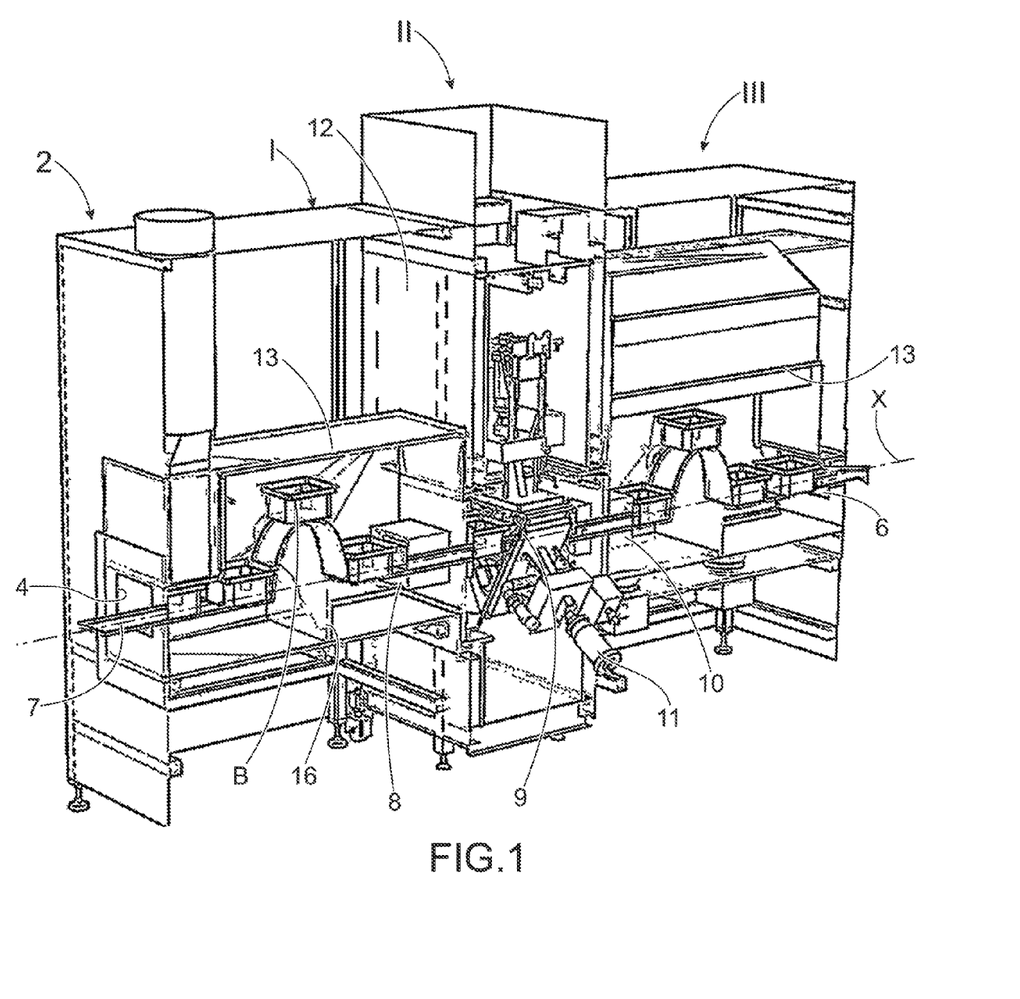
FIG. 1 is a diagrammatic view showing the operating principle of a sterilization system according to the invention.

FIG. 1 shows a diagrammatic view of the interior of a sterilization system according to one example embodiment showing the principle according to the invention.

The system comprises an envelope 2 provided with an inlet 4 and an outlet 6. Objects move along a direction X from the inlet 4 towards the outlet 6, inside the chamber 2.

Figure 2:
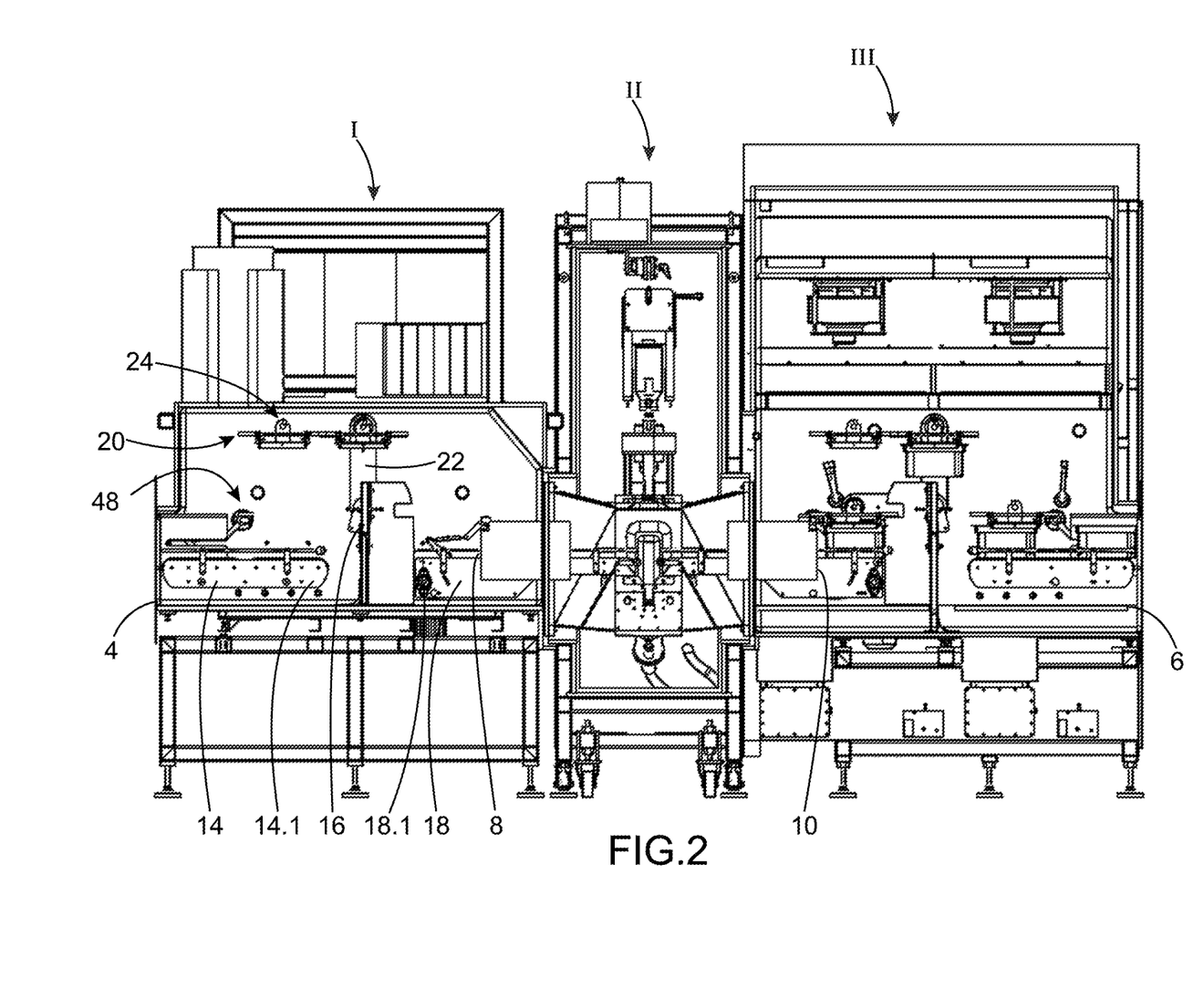
FIG. 2 is a sectional view of an example embodiment of a sterilization system.

Throughout the remainder of the description, the upstream and downstream sides are considered from the inlet towards the outlet (from the left towards the right on the view in FIGS. 1 et 2).

For example, outlet 6 is connected to an isolator (not shown).

The system has three main zones in order along the upstream to downstream direction:

a zone I, called the routing zone,
a zone II, called the treatment zone,
a zone III, called the evacuation zone.

The routing zone I extends from the inlet 4 to an inlet passage 8 to the treatment zone II, and the evacuation zone III extends from an outlet passage 10 from the treatment zone II to the outlet 6.

The sterilization system comprises a set of radiation shielding barriers that keep ionising radiation inside the envelope 2 between the inlet 4 and the outlet 6. This assembly is formed of tunnels 13 in zones I and III, a chamber that surrounds the accelerator(s) and the irradiation tunnel and is connected to the tunnels 13 through the treatment zone II inlet passage 8 and outlet passage 10, and vertical radiation shielding walls 16 in the tunnels 13 in zones I and III.

The treatment zone II comprises a conveyor 9 and one or several electron accelerators 11 that will bombard the objects passing through the system with electrons in order to sterilise their surface. In the example shown, the treatment zone II comprises three accelerators, only two of which are visible at 120° from each other around the X direction. The treatment zone II is separated from the routing zone I and the evacuation zone III by two walls 12 perpendicular to the X direction and through which the inlet passage 8 and an outlet passage 10 are formed.

The routing zone I and the evacuation zone III are similar structures, therefore only the routing zone I will be described in detail with reference to FIGS. 2 to 6.

The routing zone I is delimited by the tunnel 13 described above forming a confinement shielding for ionising radiation providing protection against radiation. The routing zone I comprises the following, in order along the upstream to downstream direction—a first conveyor 14 extending along the X direction from the inlet 4, a radiation shielding wall 16 forming shielding to confine the ionising radiation on the side of the treatment zone II and a second conveyor 18 extending along the X direction as far as the inlet passage 8 to the treatment zone II.

For example, the conveyors 14, 18 are chain link belts driven by gears or rollers that can be motor driven.

The radiation shielding wall 16 is usually made of lead. The radiation shielding wall 16 extends perpendicular to the X direction and faces the inlet passage 8.

The routing zone I also comprises means such that objects to be treated can pass over the radiation shielding wall to pass between the first conveyor 14 and the second conveyor 18.

Figure 3:
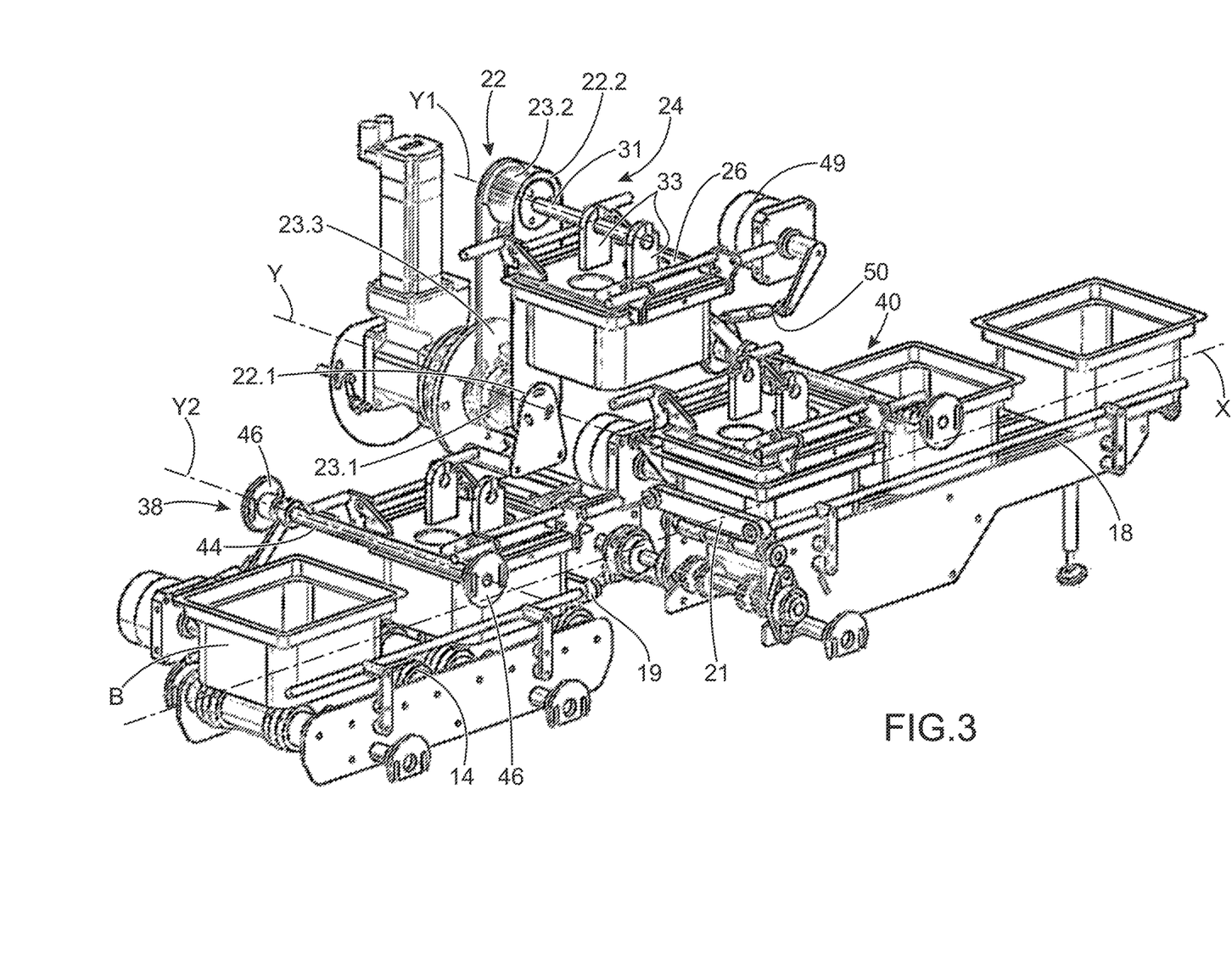
FIG. 3 is a perspective view of the upstream or downstream zone of the sterilization system in FIG. 2, in different object manipulation states.
Figure 4:
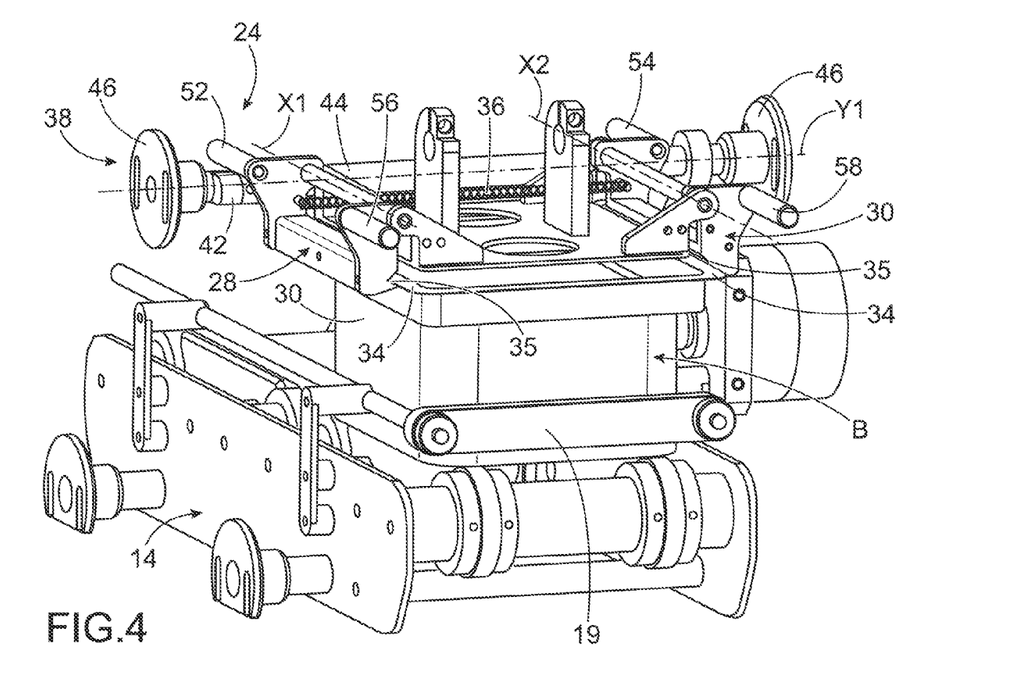
FIG. 4 is an enlarged view of part of the system in FIG. 3.

Preferably, a stop 19 is provided at the downstream end of the first conveyor 14 before the radiation shielding wall 16 to stop the object (FIG. 4). Similarly, a stop 21 is also provided at the inlet to the second conveyor 18 (FIG. 3). For example, this may be useful when the conveyors 14, 18 travel in opposite directions, the inlet to the second conveyor 18 then forming the outlet from the second conveyor.

The objects in FIG. 1 are boxes B and their trajectory in the system is shown by an arrow denoted T.

It can be seen that the boxes B move in a horizontal plane on the upstream side of the wall 16 by means of the first conveyor 14 and then move along a vertical direction and also along a horizontal direction to cross the wall 16 and then move once again in a horizontal plane downstream from the wall 16 by means of the second conveyor 18.

Since the wall is crossed from above, the length of the routing zone is shortened. The same applies for the length of the evacuation zone III.

The transverse dimension of the routing zone and evacuation zones is also shorter than in systems according to the state of the art because there is no longer a conveyor that goes around the walls horizontally.

Figure 5:
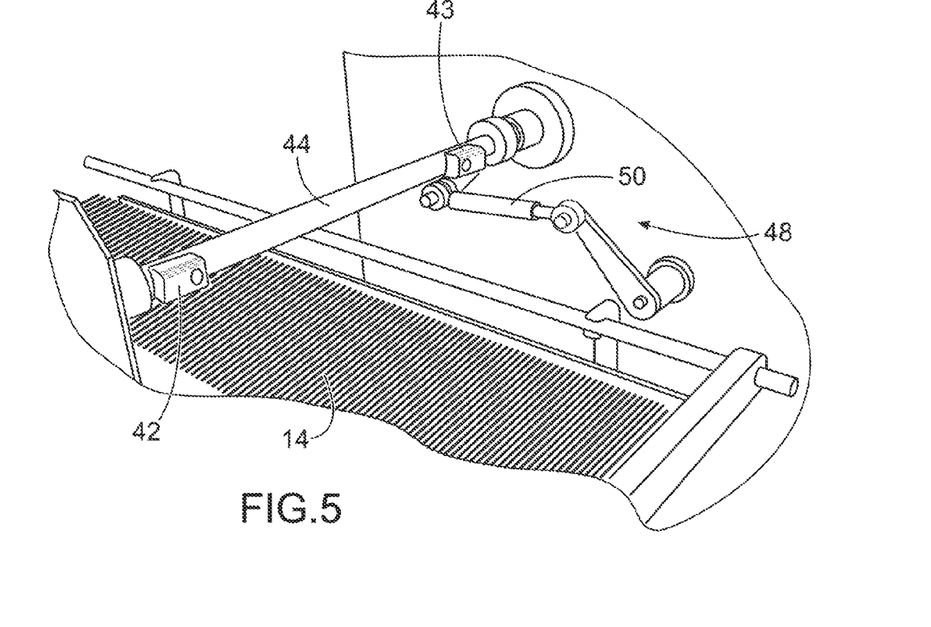
FIG. 5 is a detailed view of an actuation part of the gripping means of the crossing device.

We will now describe details of a particularly advantageous embodiment of a crossing device 20 that is visible particularly in FIGS. 3, 4 and 5.

The crossing device 20 is located between the first conveyor 14 and the second conveyor 18. It comprises an arm 22 mounted on the end of a rotation shaft 25 (FIG. 6) capable of rotating about a Y axis perpendicular to the X direction and located in a plane extending an outlet end 14.1 of the first conveyor and an inlet end 18.1 of the second conveyor 18. The arm 22 is articulated about the Y axis by a first end 22.1 and its second end 22.2 supports gripping means 24 that will grip the objects B to be treated.

For example, the drive means are composed of a motor in direct connection with the rotation shaft 25.

Advantageously, the arm 22 comprises means of keeping the gripping means and therefore the box B horizontal during the crossing.

In the example shown, these means comprise a first pulley 23.1 installed fixed relative to the entire system: the tunnel 13 and the radiation shielding walls. The rotation shaft 25 passes through the first pulley 23.1 and is free in rotation relative to the pulley 23.1. The means comprise a second pulley 23.2 installed free to rotate about the Y1 axis, a belt 23.3 connecting the two pulleys. The gripping means comprise a support 26 fixed to the pulley 23.2. Thus, the support 26 remains in its horizontal position during displacement of the arm 22.

Figure 6:
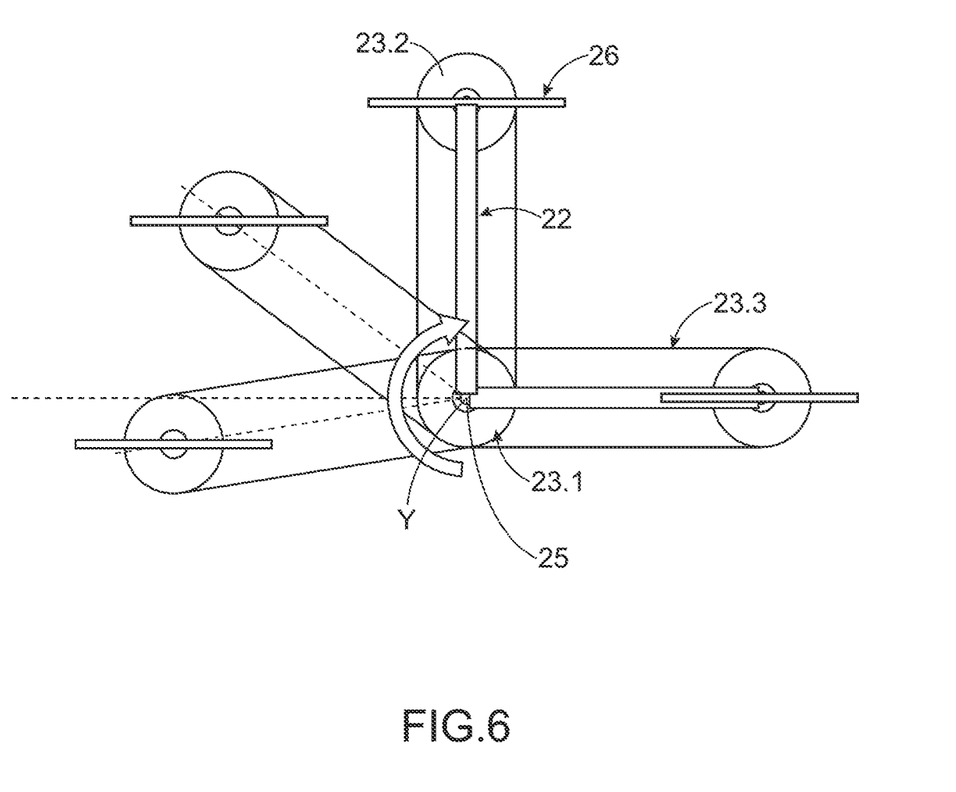
FIG. 6 is a diagrammatic view of an example of a trajectory followed by an object when it crosses over a radiation shielding wall in a sterilization system according to the invention.

FIG. 6 shows the arm in different positions as it moves between the first conveyor 14 and the second conveyor 18. The box B then follows a trajectory around an arc of a circle between the two conveyors. Manufacturing of the arm 22 and its drive have the advantage of being very simple.

As a variant, a system could be provided such that the trajectory of the box is parabolic, or even more complex. The distance between the two conveyors would then be shorter than the height to which the box has to be lifted to go over the partition 16. The length of the system would then be further reduced.

In the example shown, the gripping means 24 are adapted to grip rectangular shaped boxes.

We will now describe the shape of the boxes manipulated by the gripping means 24 in the example shown. The boxes, particularly clear in FIG. 4, are rectangular in shape. The box B is located on the conveyors 14, 18 such that its side walls 30 are parallel to the X direction. The top edge of each side wall 30 comprises a rib 34 perpendicular to the plane of the side wall towards the outside of the box and over at least part of the length of the side wall 30.

The gripping means 24 comprise the support 26 described above, on which two jaws 28, 30 are articulated about axes X1, X2 respectively. The axes X1 and X2 are parallel to the X direction. Each jaw 28, 30 comprises a groove 35 with a V profile, the axis of which is parallel to the X direction and into which a rib 34 of the top edge of a side wall 30 of the box B can fit. The support 26 is fixed in rotation to the pulley 23.2. In the example shown, an axis 31 fixed to the pulley extending along the Y1 axis is installed in two stirrups 33 fixed to the top face of the support 26 (FIG. 3).

The support 26 and therefore the transported box is kept horizontal.

Elastic return means 36 are provided between the two jaws 28, 30 to automatically return them towards each other in the gripped position. In the example shown, the elastic return means consist of a helical spring fixed at each end to a jaw 28, 30.

In the example shown and very advantageously, the gripping means 24 are actuated by external means that are not onboard the arm, which can reduce the load moved by the arm 22. However, it could be envisaged for example that the actuation means could be electrical gripping means onboard the arm, for example mounted on the support.

We will now describe the means of actuating the gripping means.

The gripping means are actuated a first time to grip the box B when it is located at the outlet 16.1 from the first conveyor 14 and a second time to release the box B when it has crossed the partition 16 and is located at the inlet 18.1 to the second conveyor 18.

Very advantageously in the example shown, the actuation means comprise a first upstream actuation part 38 to grip the box and a downstream actuation part 40 to release the box B in the upstream to downstream displacement mode. In the remainder of the description we will see that this displacement mode may be inverted.

The two upstream and downstream actuation parts 38, 40 are similar structures, therefore only the upstream actuation part 38 will be described in detail.

The upstream actuation part 38 comprises two cams 42, 43 supported by a shaft 44 located perpendicular to the X direction and at the outlet from the first conveyor 14. The shaft 44 is mounted free to rotate about an axis Y2. In the example shown, the longitudinal ends of the shaft 44 are mounted into two bearing blocks 46 fixed on the side walls of the chamber 13.

Means 48 are provided for rotating the shaft 44 about the Y2 axis, and are particularly visible in FIG. 5. In the example shown, the means 48 are offset and comprise a rotating pneumatic jack 49 (FIG. 3) that drives the shaft 44 through a rod transmission system 50.

Such rotation means 48 have a number of advantages.

Firstly, the length of the connecting rod 50 may be adjustable so that the rotation travel of the shaft 44 can be adjusted depending on the travel distance of the pneumatic jack.

Secondly, by preferably making the connecting rod 50 at least partly from a material (for example plastic) that will break under excessive mechanical stress, the remainder of the structure will be protected. The connecting rod will break preferentially before the remainder of the system. Therefore it advantageously acts as the mechanical fuse.

Finally, this embodiment enables assembly/disassembly of the shaft 44 or the jack independently of each other.

As a variant, it would be possible to install an electric motor directly at the end of the shaft 44, or to replace the rotating pneumatic jack by an electric motor.

In the example shown, the shaft 44 pivots by a quarter of a turn in one rotation direction and in the inverse rotation direction.

Each cam 42, 43 of the shaft 44 will cooperate with a pin 52, 54 supported by the jaw 28, 30 respectively, at the upstream longitudinal end of the jaw, the pins 52, 54 have longitudinal axes parallel to but distinct from the X1, X2 axes. Thus, an upwards displacement of the pin 52, 54 causes rotation of the jaw 28, 30 to which it is fixed, about its X1, X2 axis.

The jaws 28, 30 also comprise pins 56, 58 at their downstream longitudinal end that will cooperate with the actuation part 40 at the inlet to the second conveyor 18.

In another example embodiment, it would be possible to envisage eliminating the pins.

The gripping means and actuation means have the advantage that they are fully reversible, so that objects can be conveyed in the reverse direction, for example if one or several objects are trapped or jammed in the system.

Advantageously, the conveyance and irradiation procedures are controlled by a logic controller that receives signals detecting the presence of the object emitted by detectors located at different locations on the route of the conveyors, accelerator operating parameters and information from machines interfaced with the sterilization system, particularly the isolator at the outlet from the sterilization system.

We will now describe routing of a box B from the inlet 4 of the system to the outlet 6.

In FIG. 3, the gripping means 24 are shown in a state in which the box is gripped on the conveyor 14, in a state in which the box is crossing above the radiation shielding wall 16 and in a state in which the box is released on the conveyor 18.

In the initial state, the arm 22 is approximately vertical (FIG. 2).

The box B is located at the inlet 4 to the routing zone I on the downstream end of the first conveyor 14. It is then routed as far as the end 14.1 of the first conveyor 14. The presence of the box B is then detected.

The rotating arm 22 is rotated in the anticlockwise direction in FIG. 2 to position the gripping means above the box B and to position the pins 52, 54 of the jaws 28, 30 vertically in line with the cams 42, 43. The shaft 44 is then rotated by a quarter of a turn by the rod transmission system 50, which tilts the jaws 28, 30 about the X1, X2 axes. The jaws move apart, so that the top part of the box B can be positioned between the jaws 28, 30.

The rod transmission system 50 is actuated once again causing a second quarter-turn rotation of the arm 44. The cams 46 are no longer in contact with the pins 52, 54. Under the action of the return spring 36, the jaws 28, 30 move towards each other, the ribs 34 of the box B then fit into the grooves 35 of the jaws 28, 30, and the box B is then fixed to the jaws 28, 30.

The arm 22 is then pivoted in the clockwise direction so that the box B passes over the radiation shielding wall 16 and is positioned at the inlet 18.1 to the second conveyor 18.

The pins 56, 58 are then vertically in line with the cams of the downstream actuation part. The downstream rod transmission system is actuated in turn, the cams pivot and come into contact with the pins 56, 58, which has the effect of moving the jaws 28, 30 apart. The box B is then released and the box B can then be carried by the second conveyor 18 until it reaches the treatment zone II in which its external surface(s) is (are) sterilised by electron bombardment.

The box B is then taken out of the treatment zone II, and enters into the evacuation zone III. The box is then routed through the evacuation zone III in a manner similar to that in the routing zone I: displacement on a first conveyor, crossing over a radiation shielding wall by the crossing device similar to the crossing device 20, and then transported as far as the outlet 6 of the system. FIG. 2 shows the box B crossing the radiation shielding wall 16 of the evacuation zone III.

For example, when a sterilization system according to the state of the art is 4500 mm long, the sterilization system according to the invention will be 4000 mm long, which represents a substantial reduction in the length. The width of the system is also reduced, a sterilization system according to the state of the art is 4467 mm wide while the sterilization system according to the invention may be 3964 mm wide, For example, the sterilization system may be programmed to provide six treated boxes B at the outlet 6 per minute. The crossing time over the radiation shielding wall may be of the order of 3 s and the conveying speed in zones I and III is of the order of 5.4 m/min and in zone II of the order of 2 m/min.

Therefore, the sterilization system also has the advantage that it has a high supply rate of sterilised objects.

The system and particularly the gripping means have been described for the sterilization of rectangular boxes and more generally rectangular objects. It will be understood that the system is suitable for the sterilization of objects with a variety of shapes, for example such as circular boxes, the jaws then being in the shape of two arcs of a circle.

The crossing device described in detail is particularly advantageous due to its simplicity and robustness, but also to its action speed. Nevertheless, other crossing systems could also be used, for example a grab device, a magnetic device or a device with a pneumatic suction cup if the material and the shape of the objects are suitably adapted.

Furthermore, in the example described, the upstream and downstream conveyors are contained in the same horizontal plane. A system in which the upstream and downstream conveyors are in two distinct horizontal planes or in which the conveyors are in inclined planes is also within the scope of this invention.

Furthermore, a system for example in which only the routing zone or the evacuation zone comprises two conveyors and a crossing device, and the other zone comprises a single conveyor going around the side of the radiation shielding wall is not outside the scope of this invention. Such a system would also be smaller than systems according to the state of the art.

It would be possible for the routing zone and/or the evacuation zone to have several shielding walls each, the zones would then comprise as one crossing device for each wall.

What is claimed is:

1. System for sterilization of objects by electron bombardment comprising a shielded chamber to confine ionising radiation provided with an inlet and an outlet through which objects are input and output respectively, said system between the inlet and the outlet comprising a treatment zone, a routing zone upstream from the treatment zone and an evacuation zone downstream from the treatment zone, the treatment zone comprising at least one electron accelerator and a conveyor, the routing zone and the evacuation zone each including at least one radiation shielding wall protecting against ionising radiation and conveyors, the routing zone and/or the evacuation zone comprising at least a first and a second conveyor on each side of the radiation shielding wall and a device for crossing said radiation shielding wall allowing objects to pass over the radiation shielding wall passing over the top of said radiation shielding wall, in which the crossing device comprises an arm mounted at a first longitudinal end on a shaft capable of rotating about an axis perpendicular to a displacement direction of the objects, said axis being contained in a plane located between the first and the second conveyor, a gripper for gripping the objects mounted on a second longitudinal end of the arm, means of rotating the arm such that it pivots between one end of the first conveyor and one end of the second conveyor and an actuator for actuating the gripper.

2. Sterilization system according to claim 1, in which the routing zone and the evacuation zone each comprises at least one first and one second conveyor on each side of the radiation shielding wall and a device for crossing over said radiation shielding wall so that objects can pass over the radiation shielding wall above said radiation shielding wall.

3. Sterilization system according to claim 1, in which the crossing means advantageously comprise means such that the gripper moves in a succession of horizontal planes.

4. Sterilization system according to claim 3, in which said means may comprise a first fixed pulley in which the rotation shaft rotates freely, a second pulley mounted free to rotate on the second longitudinal end of the arm a belt connecting the first and second pulleys and in which the gripper is fixed in rotation to the second pulley.

5. Sterilization system according to claim 1, in which the gripper includes a support, two jaws, said jaws being hinged free to rotate on the support, each about an axis parallel to the displacement direction, elastic return means bringing the jaws back towards each other.

6. Sterilization system according to claim 1, in which the actuator is not supported by the arm.

7. Sterilization system according to claim 6, in which the actuator comprises an actuation part located at the end of the first conveyor and an actuation part located at the end of the second conveyor.

8. Sterilization system according to claim 7, in which each actuation part comprises a shaft free to rotate perpendicular to the displacement direction, said shaft being fitted with two cams, each cam being designed to cooperate with each jaw to provoke pivoting of said jaws about their axis of rotation and means of rotating the shafts by a given angle.

9. Sterilization system according to claim 8, in which each jaw comprises two pins located at each end of said jaw, said pins having a parallel axis distinct from the rotation axis of the jaw that supports it, each cam coming into contact with a pin by rotation of the shaft.

10. Sterilization system according to claim 8, in which the means of rotating the shafts by a given angle are formed by rotating pneumatic jacks connected to the shafts by rod transmission systems.

11. Sterilization system according to claim 5, in which the objects comprise two ribs and each jaw comprises a groove in which a rib will fit.

12. Sterilization system according to claim 1, comprising a detector for detecting the position of objects inside each of the zones.

13. Sterilization system according to claim 1, comprising a logic controller controlling the crossing device(s) and treatment of objects by irradiation.

14. Sterilization system according to claim 1, in which the conveyors are chain link or roller belts.

* * * * *